US007148360B2

United States Patent
Flynn et al.

(10) Patent No.: US 7,148,360 B2
(45) Date of Patent: Dec. 12, 2006

(54) PERFLUOROPOLYETHER BENZOTRIAZOLE COMPOUNDS

(75) Inventors: Richard M. Flynn, Mahtomedi, MN (US); Naiyong Jing, Woodbury, MN (US); Mark J. Pellerite, Woodbury, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 321 days.

(21) Appl. No.: 10/769,024

(22) Filed: Jan. 30, 2004

(65) Prior Publication Data

US 2005/0166791 A1    Aug. 4, 2005

(51) Int. Cl.
    *C07D 249/12*    (2006.01)
(52) U.S. Cl. .................................... 548/264.6
(58) Field of Classification Search .............. 548/264.6
    See application file for complete search history.

(56) References Cited

U.S. PATENT DOCUMENTS

| 3,350,808 | A | 11/1967 | Mitchell |
| 3,413,227 | A | 11/1968 | Howard et al. |
| 4,788,292 | A | 11/1988 | Clark et al. |
| 5,504,214 | A | 4/1996 | Marhold et al. |
| 5,851,674 | A | 12/1998 | Pellerite et al. |
| 6,344,454 | B1 * | 2/2002 | Lehmann et al. ........ 514/230.5 |
| 6,376,065 | B1 | 4/2002 | Korba et al. |
| 6,548,534 | B1 * | 4/2003 | Lehmann et al. ........... 514/435 |

FOREIGN PATENT DOCUMENTS

| EP | 0 256 978 | 2/1988 |
| WO | WO 99/37626 | 7/1999 |
| WO | WO 03/102003 | 12/2003 |

OTHER PUBLICATIONS

Flynn et al., U.S. Appl. No. 60/496,837, "Perfluoropolyether Amide-linked Phosphonates, Phosphates, and Derivatives Thereof", filed Aug. 21, 2003.

* cited by examiner

*Primary Examiner*—Joseph K. McKane
*Assistant Examiner*—Susannah L. Chung
(74) *Attorney, Agent, or Firm*—Jean A. Lown

(57) ABSTRACT

Perfluoropolyether benzotriazole compounds and compositions containing perfluoropolyether benzotriazole compounds are provided. The perfluoropolyether benzotriazole compounds can be attached to a substrate having a metal or metal oxide-containing surface to provide at least one of the following characteristics: anti-soiling, anti-staining, ease of cleaning, repellency, hydrophobicity, or oleophobicity.

13 Claims, No Drawings

PERFLUOROPOLYETHER BENZOTRIAZOLE COMPOUNDS

BACKGROUND

Common causes of electronic device failures are microcracks or voids that form in a part of the electronic device, such as a semiconductor chip, particularly in stressful environments. Such microcracks or voids can allow introduction of impurities into the electronic device. Application of a sputtered metal or metal oxide coating on electronic devices can provide a barrier against microcrack or void development. Such a sputtered coating can provide a barrier against introduction of ionic impurities, such as chloride ion and sodium ion that can disrupt transmission of electronic signals. Application of such a sputtered coating to the electronic device can also provide some protection against moisture and volatile organic chemicals.

Other articles can have an outer layer or coating of metal or metal oxides. For example, various optical substrates can be coated with one or more layers of metal oxides to reduce glare and reflection of light. Such optical substrates include those used in doors, windows, picture frames, optical lenses, filters, display devices (e.g., display panels of electronic devices), and the like.

Metal or metal oxide coatings are generally durable and uniform. However, some metal or metal oxide layers made by common techniques, such as sputtering processes, are relatively porous and contain clusters of particles that form a relatively rough profile. Sputtered metal or metal oxide coatings tend to have a high surface energy making these materials prone to contamination by impurities from a variety of potential sources such as fingerprints. Articles having such coatings can be difficult to clean without the use of solvent-based cleaners, some of which are environmentally undesirable. Additionally, removal of surface contaminants can detrimentally affect desired properties of the metal or metal oxide surface if the cleaning process leaves residue behind.

Numerous attempts have been made to provide anti-soiling characteristics to metal or metal oxide surfaces. Some attempts have focused on providing these characteristics to the metal or metal oxide layer itself, while other attempts have focused on providing an anti-soiling coating over the metal or metal oxide surface. Such anti-soiling overcoats can be monolayer films that are free of low molecular weight impurities. Low molecular weight or soft materials are generally considered undesirable because these materials can adversely affect the anti-soiling characteristics of the overcoat. Some existing overcoats that are capable of providing adequate anti-soiling characteristics to electronic components include compounds that are based on seven-carbon and eight-carbon perfluoroalkyl groups. However, some of these compounds are losing favor as possibly being environmentally undesirable.

The technique for applying the anti-soiling overcoat to the substrate can also be problematic, depending on the composition of the particular overcoat. For example, conventional application methods for some anti-soiling overcoats entail application of excess coating material that is removed to maintain desirable characteristics of the metal or metal oxide-containing substrate. Such methods typically require a post-treatment step such as polishing or solvent washing. In general, such post-treatment steps are undesirable to manufacturers because such post-treatment steps can increase costs, can involve use of additional solvents, can increase the chance of degrading the metal or metal oxide-containing substrate, or combinations thereof.

SUMMARY

Perfluoropolyether benzotriazole compounds and compositions containing perfluoropolyether benzotriazole compounds are provided. The perfluoropolyether benzotriazole compounds can be attached to a substrate to provide at least one of the following characteristics: anti-soiling, anti-staining, ease of cleaning, repellency, hydrophobicity, oleophobicity, or tarnish resistance.

In one aspect, perfluoropolyether benzotriazole compounds are provided according to Formula I:

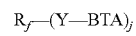

$$R_f\text{—(Y—BTA)}_j \qquad \text{I}$$

where $R_f$ is a monovalent or divalent perfluoropolyether group; Y is a covalent bond or a divalent organic linking group selected from an alkylene, arylene, heteroalkylene, carbonyl, carbonyloxy, carbonylimino, sulfonamido, or combinations thereof wherein an alkylene, arylene, or heteroalkylene group can be unsubstituted or substituted with an alkyl, aryl, halo, or combinations thereof; j is 1 or 2; and BTA a monovalent benzotriazolyl group having one of the following structures:

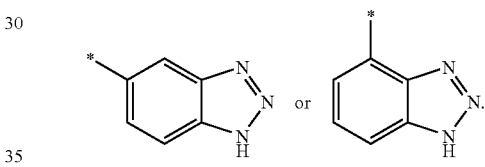

The benzotriazolyl group can be unsubstituted or substituted with an alkyl, alkoxy, or a combination thereof. An asterisk indicates where the benzotriazolyl group is attached to the rest of the compound.

Another aspect provides compositions that include a perfluoropolyether benzotriazole compound of Formula I and a solvent. In some embodiments, the solvent is selected from an alcohol, hydrofluoroether, or a combination thereof.

Other aspects provide an article and a method of preparing an article. The article includes a substrate and a perfluoropolyether benzotriazole compound of Formula I attached to the surface of the substrate.

Yet another aspect provides a method of treating a substrate by applying a coating composition that includes applying a coating composition to the surface of a substrate. The coating composition includes a perfluoropolyether benzotriazole compound of Formula I.

The above summary is not intended to describe each disclosed embodiment or every implementation of the present invention. The detailed description section that follows more particularly exemplifies these embodiments.

DETAILED DESCRIPTION

Perfluoropolyether benzotriazole compounds and compositions containing perfluoropolyether benzotriazole compounds are provided. Additionally, articles, methods of making articles, and methods of treating a substrate are described.

Definitions

As used herein, the terms "a", "an", and "the" are used interchangeably with "at least one" or more of the elements being described.

As used herein, the term "acyl" refers to a group of formula R(CO)— where (CO) indicates that the carbon is attached to the oxygen with a double bond and R is an alkyl group.

As used herein, the term "alcohol" refers to a compound of formula ROH where R is an alkyl group.

As used herein, the term "alkane" refers to saturated hydrocarbons. The alkane can have a linear structure, branched structure, cyclic structure, or combinations thereof. The alkane typically has one to thirty carbon atoms. In some embodiments, the alkane has one to twenty, one to ten, one to eight, one to six, one to four, or one to three carbon atoms.

As used herein, the term "alkoxy" refers to a group of formula —OR where R is an alkyl group.

As used herein, the term "alkyl" refers to a monovalent moiety formed by abstraction of a hydrogen atom from an alkane. The alkyl can have a linear structure, branched structure, cyclic structure, or combinations thereof. A cycloalkyl is a cyclic alkyl and is a subset of an alkyl group.

As used herein, the term "alkylene" refers to a divalent moiety formed by abstraction of two hydrogen atoms from an alkane. The alkylene can have a linear structure, branched structure, cyclic structure, or combinations thereof.

As used herein, the term "aryl" refers to a monovalent moiety of a carbocyclic aromatic compound having one to five connected rings, multiple fused rings, or combinations thereof. In some embodiments, the aryl group has four rings, three rings, two rings, or one ring. For example, the aryl group can be phenyl.

As used herein, the term "arylene" refers to a divalent moiety of a carbocyclic aromatic compound having one to five connected rings, multiple fused rings, or combinations thereof. In some embodiments, the arylene group has four rings, three rings, two rings, or one ring. For example, the arylene group can be phenylene.

As used herein, the term "carbonyl" refers to a divalent group of formula —(CO)— where the carbon is attached to the oxygen with a double bond.

As used herein, the term "carbonyloxy" refers to a divalent group of formula —(CO)O—.

As used herein, the term "carbonylimino" refers to a divalent group of formula —(CO)NR$^d$—, where R$^d$ is hydrogen or alkyl.

As used herein, the term "fluoroalkyl" refers to an alkyl group in which at least one of the hydrogen atoms is replaced with a fluorine atom.

As used herein, the term "fluoroether" refers to a compound or group having two saturated or unsaturated hydrocarbon groups linked with an oxygen atom (i.e., there is one catenated oxygen atom). At least one of the hydrocarbon groups has at least one hydrogen atom replaced with a fluorine atom. The hydrocarbon groups can have a linear structure, branched structure, cyclic structure, or combinations thereof.

As used herein, the term "fluoropolyether" refers to a compound or group having three or more saturated or unsaturated hydrocarbon groups linked with oxygen atoms (i.e., there are at least two catenated oxygen atoms). At least one, and typically two or more, of the hydrocarbon groups has at least one hydrogen atom replaced with a fluorine atom. The hydrocarbon groups can have a linear structure, branched structure, cyclic structure, or combinations thereof.

As used herein, the term "halo" refers to chlorine, bromine, or fluorine.

As used herein, the term "heteroalkane" refers to an alkane having one or more carbon atoms replaced with a sulfur, oxygen, or NR$^d$ where R$^d$ is hydrogen or alkyl. The heteroalkane can have a linear structure, branched structure, cyclic structure, or combinations thereof. In some embodiments, the heteroalkane includes no more than twenty carbon atoms, no more than ten carbon atoms, no more than eight carbon atoms, no more than six carbon atoms, or no more than four carbon atoms. Ethers and polyethers are subsets of a heteroalkane.

As used herein, the term "heteroalkyl" refers to a monovalent moiety formed by abstraction of a hydrogen atom from a heteroalkane.

As used herein, the term "heteroalkylene" refers to a divalent moiety formed by abstraction of two hydrogen atoms from a heteroalkane.

As used herein, the term "perfluoroalkane" refers to an alkane in which all of the hydrogen atoms are replaced with fluorine atoms.

As used herein, the term "perfluoroalkanediyl" refers to a divalent moiety formed by abstraction of two fluorine atoms from a perfluoroalkane where the radical centers are located on different carbon atoms.

As used herein, the term "perfluoroalkanetriyl" refers to a trivalent moiety formed by abstraction of three fluorine atoms from a perfluoroalkane.

As used herein, the term "perfluoroalkyl" refers to an alkyl group in which all of the hydrogen atoms are replaced with fluorine atoms.

As used herein, the term "perfluoroalkylidene" refers to a divalent moiety formed by abstraction of two fluorine atoms from a perfluoroalkane where the radical centers are on the same carbon atom.

As used herein, the term "perfluoroalkoxy" refers to an alkoxy group in which all of the hydrogen atoms are replaced with fluorine atoms.

As used herein, the term "perfluoroether" refers to a fluoroether in which all of the hydrogens on all of the hydrocarbon groups are replaced with fluorine atoms.

As used herein, the term "perfluoropolyether" refers to a fluoropolyether in which all of the hydrogens on all of the hydrocarbon groups are replaced with fluorine atoms.

As used herein, the term "sulfonamido" refers to a group of formula —SO$_2$NR$^a$— where R$^a$ is hydrogen, alkyl or aryl.

As used herein, an asterisk ("*") indicates the location where a group or moiety is attached to the rest of a compound.

Compounds

Perfluoropolyether benzotriazole compounds are provided according to Formula I:

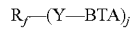

$$R_f—(Y—BTA)_j \qquad \text{I}$$

where $R_f$ is a monovalent or divalent perfluoropolyether group; Y is a covalent bond or a divalent organic linking group selected from an alkylene, arylene, heteroalkylene, carbonyl, carbonyloxy, carbonylimino, sulfonamido, or combinations thereof wherein an alkylene, arylene, or heteroalkylene group can be unsubstituted or substituted with an alkyl, aryl, halo, or combinations thereof; j is 1 or 2; and BTA is a monovalent benzotriazolyl group having one of the following structures:

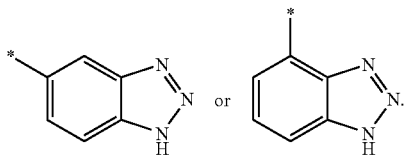

The benzotriazolyl group can be unsubstituted or substituted with an alkyl, alkoxy, or a combination thereof.

The perfluoropolyether group $R_f$ in the compounds according to Formula I can have a linear structure, branched structure, cyclic structure, or combinations thereof. Additionally, the perfluoropolyether group $R_f$ can be saturated or unsaturated. The perfluoropolyether group $R_f$ has at least two catenary oxygen atoms and can be monovalent (i.e., j is equal to 1 in Formula I) or divalent (i.e., j is equal to 2 in Formula I). In many compounds, j is equal to 1.

Exemplary perfluoropolyether groups $R_f$ in compounds according to Formula I include, but are not limited to, perfluoropolyether groups that have perfluorinated repeating units selected from —$(C_pF_{2p})$—, —$(C_pF_{2p}O)$—, —$(CF(Z)O)$—, —$(CF(Z)C_pF_{2p}O)$—, —$(C_pF_{2p}CF(Z)O)$—, —$CF_2CF(Z)O$—, or combinations thereof. In these repeating units, p is typically an integer ranging from 1 to 10. In some embodiments, p is an integer of 1 to 8, 1 to 6, 1 to 4, or 1 to 3. The group Z in some of the depicted perfluorinated repeating units can be a perfluoroalkyl group, a perfluoroether group, a perfluoropolyether group, or a perfluoroalkoxy group. The group Z can have a linear structure, branched structure, cyclic structure, or combinations thereof. The group Z typically has no more than twelve carbon atoms, no more than ten carbon atoms, no more than nine carbon atoms, no more than four carbon atoms, no more than three carbon atoms, no more than two carbon atoms, or no more than one carbon atom. In some embodiments, the group Z has no more than four oxygen atoms, no more than three oxygen atoms, no more than two oxygen atoms, no more than one oxygen atom, or no oxygen atoms. In some compounds, the $R_f$ group has one perfluorinated repeating unit. In other compounds, different perfluorinated repeating units are combined in a block or random arrangement to form the $R_f$ group.

Where the perfluoropolyether group $R_f$ is monovalent, the terminal group of the perfluoropolyether group $R_f$ can be $(C_pF_{2p+1})$—, $(C_pF_{2p+1}O)$—, $(X'C_pF_{2p}O)$—, or $(X'C_pF_{2p})$—, for example, where X' can be hydrogen, chlorine, or bromine; and p is an integer of 1 to 10, 1 to 8, 1 to 6, 1 to 4, or 1 to 3. Some exemplary monovalent perfluoropolyether groups $R_f$ include, but are not limited to, $C_3F_7O(CF(CF_3)CF_2O)_nCF(CF_3)$—, $C_3F_7O(CF_2CF_2CF_2O)_nCF_2CF_2$—, and $CF_3O(C_2F_4O)_nCF_2$— wherein n has an average value of 0 to 50, 1 to 50, 3 to 30, 3 to 15, 3 to 10.

Other exemplary monovalent perfluoropolyether groups $R_f$ include, but are not limited to $CF_3O(CF_2O)_q(C_2F_4O)_nCF_2$— and $F(CF_2)_3O(C_4F_8O)_n(CF_2)_3$—, where q can have an average value of 0 to 50, 1 to 50, 3 to 30, 3 to 15, or to 10; and n can have an average value of 0 to 50, 3 to 30, 3 to 15, or 3 to 10.

Some exemplary divalent perfluoropolyether groups $R_f$ include, but are not limited to —$CF_2O(CF_2O)_q(C_2F_4O)_nCF_2$—, —$CF_2O(C_2F_4O)_nCF_2$—, —$(CF_2)_3O(C_4F_8O)_n(CF_2)_3$—, and —$CF(CF_3)(OCF_2CF(CF_3))_sOC_tF_{2t}O(CF(CF_3)CF_2O)_nCF(CF_3)$— where q can have an average value of 0 to 50, 1 to 50, 3 to 30, 3 to 15, or 3 to 10; n can have an average value of 0 to 50, 3 to 30, 3 to 15, or 3 to 10; s can have an average value of 0 to 50, 1 to 50, 3 to 30, 3 to 15, or 3 to 10; the sum of n and s (i.e., n+s) can have an average value of 0 to 50 or 4 to 40; the sum of q and n (i.e., q+n) can be greater than 0; and t can be an integer of 2 to 6.

As synthesized, the perfluoropolyether benzotriazole compounds according to Formula I typically are mixtures having different perfluoropolyether groups $R_f$ (i.e., the compound is not synthesized as a single compound but a mixture of compounds with different $R_f$ groups). For example, the values of q, n, and s can vary as long as the mixture has a number average molecular weight of at least 400 g/mole. Suitable perfluoropolyether benzotriazole mixtures typically have a number average molecular weight of at least about 400, at least 800, or at least about 1000 g/mole. Mixtures of different perfluoropolyether benzotriazole compounds often have a molecular weight (number average) of 400 to 10000 g/mole, 800 to 4000 g/mole, or 1000 to 3000 g/mole.

The linking group Y in the compounds according to Formula I can be a single covalent bond or a divalent organic group selected from alkylene, arylene, heteroalkylene, carbonyl, carbonyloxy, carbonylimino, sulfonamido, or combinations thereof. Any alkylene, arylene, or heteroalkylene included in the linking group Y can be unsubstituted or, alternatively, can be substituted with an alkyl, an aryl, a halo, or combinations thereof. An alkyl or alkoxy substituent usually has up to 10, up to 6, or up to 4 carbon atoms.

The linking group Y typically has no more than 30 carbon atoms. In some compounds, the linking group Y has no more than 20 carbon atoms, no more than 10 carbon atoms, no more than 6 carbon atoms, or no more than 4 carbon atoms. Some exemplary Y groups include, but are not limited to, —(CO)NR$^d$—, —(CO)O—, —C$_k$H$_{2k}$O(CO)—, —(CO)NR$^d$—C$_k$H$_{2k}$—(CO)O—, —(CO)NR$^d$—C$_k$H$_{2k}$—(CO)NR$^d$—, —(CO)NR$^d$—C$_k$H$_{2k}$—O(CO)—, —(CO)O—C$_k$H$_{2k}$—(CO)O—, —(CO)O—C$_k$H$_{2k}$—(CO)NR$^d$—, —(CO)NR$^d$—Ar—(CO)O—, —(CO)NR$^d$—Ar—(CO)NR$^d$—, —(CO)NR$^d$—Ar—O(CO)—, —(CO)O—Ar—(CO)O—, —(CO)O—Ar—(CO)NR$^d$—, or —(CO)—Ar—O(CO)— where Ar is an arylene (e.g., phenylene), k is an integer of 1 to 10, and R$^d$ is hydrogen or an alkyl.

In some compounds Y is selected from carbonyloxy, carbonylimino, and alkylene. The alkylene can be unsubstituted or substituted with an alkyl, alkoxy, halo, or combinations thereof. Examples include, but are not limited to, —(CO)NR$^d$—, —(CO)O—, —C$_k$H$_{2k}$O(CO)—, —(CO)NR$^d$—C$_k$H$_{2k}$—(CO)O—, —(CO)NR$^d$—C$_k$H$_{2k}$—(CO)NR$^d$—, —(CO)NR$^d$—C$_k$H$_{2k}$—O(CO)—, —(CO)O—C$_k$H$_{2k}$—(CO)O—, or —(CO)O—C$_k$H$_{2k}$—(CO)NR$^d$— where k is an integer of 1 to 10 and R$^d$ is hydrogen or an alkyl. Some exemplary Y groups include —CH$_2$O(CO)—(CO)NR$^d$CH$_2$CH$_2$O(CO)—, —(CO)NR$^d$CH$_2$CH$_2$O(CO)—, and —(CO)NR$^d$CH$_2$CH$_2$NR$^d$(CO)— where R$^d$ is hydrogen or alkyl (e.g., an alkyl having 1 to 10 carbon atoms). More specific examples of Y include, but are not limited to, —(CO)NH—, —CH$_2$O(CO)—, —(CO)NH—C$_2$H$_4$—(CO)O—, —(CO)NH—C$_2$H$_4$—(CO)NH—, —(CO)NH—C$_2$H$_4$—O(CO)—, —(CO)O—C$_2$H$_4$—(CO)O—, —(CO)O—C$_2$H$_4$—(CO)NH—, —(CO)N(CH$_3$)—, —(CO)N(CH$_3$)—C$_2$H$_4$—O(CO)—, and —(CO)N(CH$_3$)—C$_2$H$_4$—(CO)NH—.

In some embodiments, the benzotriazolyl group is unsubstituted (e.g., the benzene ring is not substituted with an alkyl or alkoxy group). In other embodiments, the benzotriazolyl group is substituted with an alkyl or alkoxy group. An alkyl or alkoxy substituent can have up to 10, up to 6, or up to 4 carbon atoms.

Some examples of compounds falling within the scope of the compounds represented by Formula I include the compounds represented by Formula II, Formula III, Formula IV, and Formula V below:

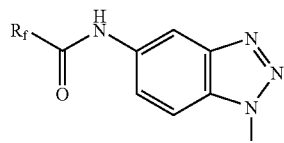

II

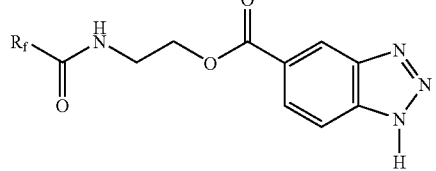

III

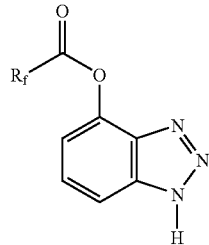

IV

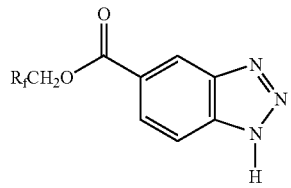

V where $R_f$ is a monovalent perfluoropolyether group as described above.

Some more specific examples of compounds according to Formula I and Formula II include the compounds represented by Formula VI below:

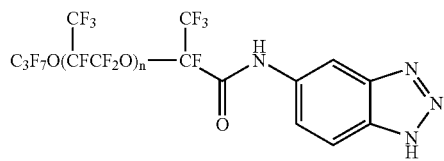

VI where n can have an average value of 0 to 50, 1 to 50, 3 to 30, 3 to 15, or 3 to 10. In some compounds according to Formula VI, n has an average value of at least 3, at least 4, or at least 5.

Some more specific examples of compounds according to Formula I and Formula III include the compounds represented by Formula VII below:

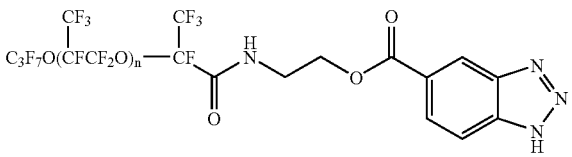

VII where n can have an average value of 0 to 50, 1 to 50, 3 to 30, 3 to 15, or 3 to 10. In some compounds according to Formula VII, n has an average value of at least 3, at least 4, or at least 5.

Compositions

Compositions are provided that include a solvent and a perfluoropolyether benzotriazole compound according to Formula I:

$$R_f—(Y—BTA)_j \qquad \text{I}$$

where $R_f$ is a monovalent or divalent perfluoropolyether group; Y is a covalent bond or a divalent organic linking group selected from an alkylene, arylene, heteroalkylene, carbonyl, carbonyloxy, carbonylimino, sulfonamido, or combinations thereof wherein an alkylene, arylene, or heteroalkylene group is unsubstituted or substituted with an alkyl, aryl, halo, or combinations thereof; j is 1 or 2; and BTA is a monovalent benzotriazolyl group having one of the following structures:

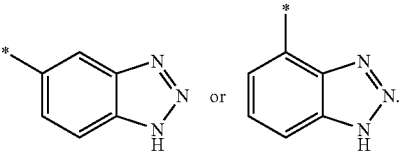

The benzotriazolyl group can be unsubstituted or substituted with an alkyl, alkoxy, or a combination thereof. Other details about the perfluoropolyether group $R_f$, about the linking group Y, and about the perfluoropolyether benzotriazole compounds depicted by Formula I are described above.

A solvent suitable for dissolving or dispersing the benzotriazole compounds can be used as the solvent. In some embodiments, the solvents substantially completely dissolve compounds according to Formula I. Examples of appropriate solvents include, but are not limited to, alcohols (e.g., methanol, ethanol, 1-propanol, 2-propanol, 2-methyl-2-propanol, 1-butanol, and 2-butanol), esters, ketones (e.g., ethyl acetate and acetone), fluorinated hydrocarbons (e.g., fluorine-substituted alkanes), ethers (e.g., hydrofluoroethers and hydrochlorofluoroethers), and hydrochlorofluoro alkanes. Mixtures of such solvents can be used. In some applications, the solvent is an alcohol, hydrofluoroether, or a combination thereof.

Suitable hydrofluoroethers, for example, can fall within the scope of Formula VIII:

$$R_f^1\text{—[O—}R_h]_a \qquad \text{VIII}$$

where a is an integer of 1 to 3, the group $R_f^1$ is a monovalent, divalent, or trivalent moiety of a perfluoroalkane, perfluoroether, or perfluoropolyether; and $R_h$ is an alkyl or heteroalkyl. The $R_f^1$ group can have a linear structure, branched structure, cyclic structure, or combinations thereof. Likewise, the $R_h$ group can have a linear structure, branched structure, cyclic structure, or combinations thereof. The sum of the number of carbon atoms in the group $R_f^1$ and the number of carbon atoms in the group $R_h$ will typically be greater than or equal to four.

The $R_f^1$ group is monovalent when a is equal to 1, divalent when a is equal to 2, and trivalent when a is equal to 3. The $R_f^1$ group typically contains no more than 30 carbon atoms, no more than 20 carbon atoms, no more than 15 carbon atoms, no more than 12 carbon atoms, or no more than 8 carbon atoms. The $R_f^1$ group can include at least 1, at least 2, at least 3, or at least 4 carbon atoms. In some applications $R_f^1$ includes 4 to 9 carbon atoms, 4 to 8, 4 to 7, 5 to 7, or 5 to 6 carbon atoms. For a divalent $R_f^1$ group, the radical centers can be on the same or different carbon atoms. For a trivalent $R_f^1$ group, the radical centers can each be on a different carbon atom or two of the radical centers can be on the same carbon atom.

In some compounds according to Formula VIII where a is equal to 1, the group $R_f^1$ can, for example, be (1) a linear or branched perfluoroalkyl group having from two to about fifteen carbon atoms, (2) a perfluorocycloalkyl-containing perfluoroalkyl group having from five to about fifteen carbon atoms, or (3) a perfluorocycloalkyl group having from three to about twelve carbon atoms. A cyclic structure can be optionally substituted with a perfluoroalkyl group having 1 to 4 carbon atoms.

In some compounds according to Formula VIII where a is equal to 2, the group $R_f^1$ can be (1) a linear or branched perfluoroalkanediyl group, (2) a perfluoroalkylidene group having from two to about fifteen carbon atoms, (3) a perfluorocycloalkyl- or perfluorocycloalkylene-containing perfluoroalkanediyl or perfluoroalkylidene group having from five to about fifteen carbon atoms, or (4) a perfluorocycloalkanediyl group or perfluorocycloalkylidene group having from three to about twelve carbon atoms. A cyclic structure can be optionally substituted with a perfluoroalkyl group having 1 to 4 carbon atoms.

In some compounds according to Formula VIII when a is equal to 3, the group $R_f^1$ can be (1) a linear or branched perfluoroalkanetriyl group having from two to about fifteen carbon atoms, (2) a perfluorocycloalkyl- or perfluorocycloalkylene-containing group from about six to fifteen carbon atoms, or (3) a perfluorocycloalkanetriyl group having from three to about twelve carbon atoms. A cyclic structure can be optionally substituted with a perfluoroalkyl group having 1 to 4 carbon atoms.

In compounds according to Formula VIII, each $R_h$ group can independently be an alkyl or a heteroalkyl. Each of the groups usable as $R_h$ can have a linear structure, branched structure, cyclic structure, or combinations thereof. In some embodiments where $R_h$ is a heteroalkyl group, the heteroalkyl moiety can be an ether group or a polyether group. The alkyl or heteroalkyl group used as the group $R_h$ often will have no more than twenty carbon atoms, no more than ten carbon atoms, or no more than eight carbon atoms. In some compounds according to Formula VIII, the $R_h$ group can have one to eight carbon atoms. For example, the group $R_h$ in the compounds according to Formula VIII can be a cycloalkyl-containing alkyl group having from four to about eight carbon atoms or a cycloalkyl group having from three to about eight carbon atoms.

Some specific exemplary hydrofluoroethers that fall within the scope of the compound according to Formula VIII include, but are not limited to, methyl perfluoro-n-butyl ether, methyl perfluoroisobutyl ether, ethyl perfluoro-n-butyl ether, ethyl perfluoroisobutyl ether, or combinations thereof.

Synthesis of Perfluoropolyether Benzotriazole Compounds

Perfluoropolyether benzotriazole compounds according to Formula I can generally be synthesized by reacting (a) a benzotriazole, such as a carboxylic acid benzotriazole, an amino-benzotriazole, a benzotriazole alcohol, or a benzotriazole ester, with (b) a perfluoropolyether containing a functional group, such as a perfluoropolyether acyl halide, a perfluoropolyether amido alcohol, or a perfluoropolyether alcohol. The reaction is generally carried out in solution with the benzotriazole and the perfluoropolyether being dissolved (or dispersed) in a suitable solvent. Useful solvents include triethylamine, tetrahydrofuran, N,N-dimethylformamide, t-butyl methyl ether, and any mixture of these. The reaction can be conducted at a temperature ranging from about 20° C. to about 50° C. to yield a mixture containing the product. The product can optionally be subjected to a suitable process, such as rotary evaporation, to remove residual solvent. The product can also be optionally purified using known techniques such as, for example, fractional distillation or solvent dissolution followed by precipitation.

Some exemplary reaction sequences for producing perfluoropolyether benzotriazole compounds according to Formula I, and specifically for producing perfluoropolyether benzotriazole compounds according to Formulas II, III, IV, and V, are provided below as Reaction Sequences A, B, C, and D, respectively.

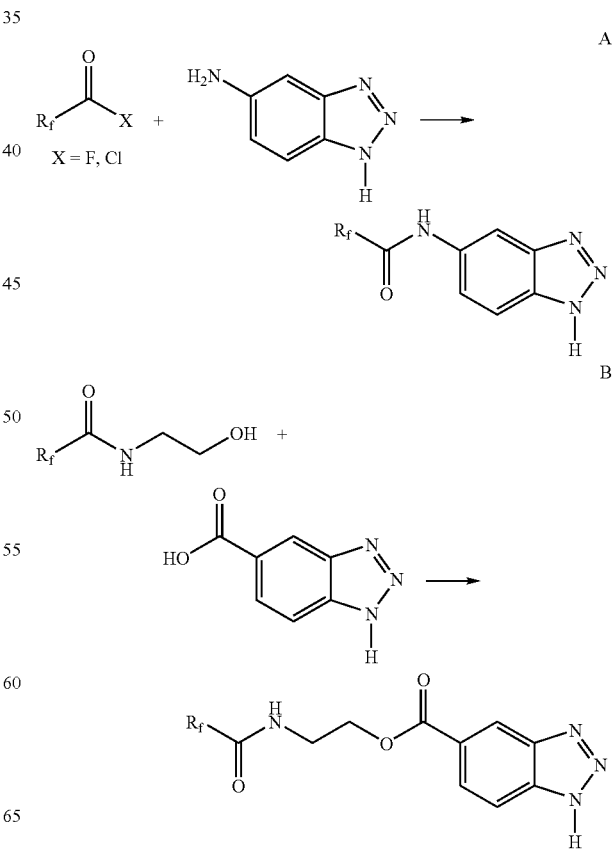

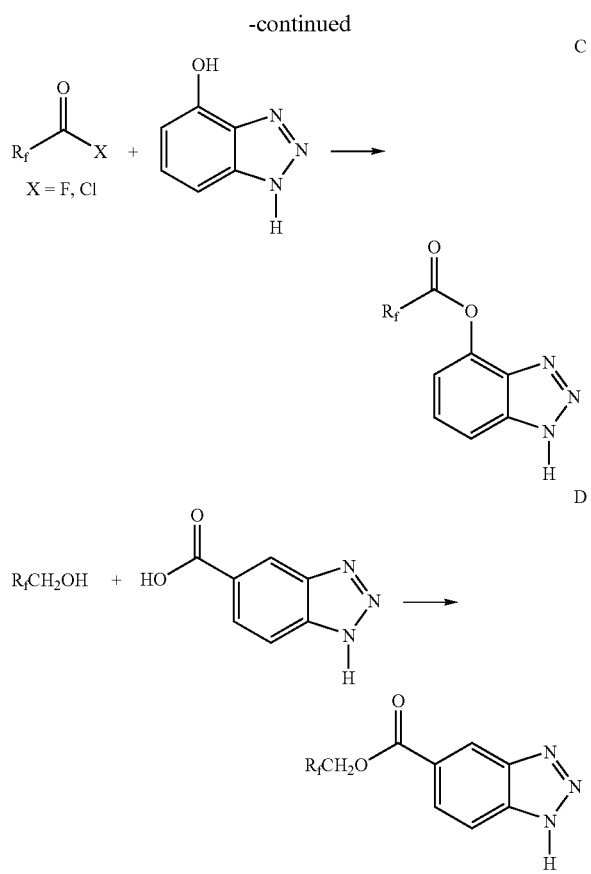

where $R_f$ is a monovalent perfluoropolyether group.

Articles and Methods of Using Perfluoropolyether Benzotriazole Compounds

Another aspect of the invention provides an article that includes a substrate and a compound according to Formula I attached to a surface of the substrate. The compound according to Formula I is the same as described above. In some embodiments, the compounds of Formula I are attached to one surface of the substrate. In other embodiments, the compounds of Formula I are attached to two or more surfaces of the substrate (e.g., the compounds of Formula I can be attached to all surfaces of the substrate).

Yet another aspect of the invention provides a method of making an article that includes applying a coating composition to a surface of a substrate. The coating composition includes a compound according to Formula I. In some embodiments, the coating composition includes a solvent as well as a compound according to Formula I. The compound according to Formula I is the same as described above. The solvent can be selected, for example, from an alcohol, hydrofluoroether, or a combination thereof.

The substrates are any suitable solid support capable of adsorbing or forming a bond with the perfluoropolyether benzotriazole compounds of Formula I. The substrate can be porous or non-porous, rigid or flexible, transparent or opaque, colorless or colored, and reflective or non-reflective. The substrate can be a single layer of material or can include multiple layers of material.

In some embodiments, the substrate includes a base layer and a metal-containing layer on at least one surface of the base layer. The base layer can be prepared from a glass, ceramic, polymeric material, metal, metal oxide, or combinations thereof. The metal-containing layer can include metals, metal oxides, or a combination thereof. Exemplary metal-containing layers can include gold, platinum, chromium, aluminum, copper, silver, titanium, indium, germanium, tin, nickel, indium tin, or combinations thereof. Many metal surfaces contain at least some metal oxides. In some applications, the metal-containing layer includes metal oxides such as chromium oxide, aluminum oxide, copper oxide, silver oxide, titanium oxide, indium oxide, germanium oxide, tin oxide, nickel oxide, indium tin oxide, or combinations thereof.

A coating that includes a compound according to Formula I can be applied to the surface of the substrate to provide an article having a low energy surface. The coatings can render a substrate surface more resistant to contamination by inhibiting dirt, other particles, and skin oils from fingerprints, for example, from adhering to the surface of the substrate. The coating, at least in some embodiments, can render the surface of the substrate easier to clean with dry wiping or with a solvent. Suitable cleaning solvents include, but are not limited to, water, methanol, ethanol, isopropanol, acetone, methyl ethyl ketone, or a fluorinated solvent such as perfluorocarbon or a hydrofluoroether. The coating can usually withstand multiple cleanings without deleteriously affecting the beneficial properties of the coating of a compound according to Formula I.

In some application, the substrate is an electronic component, such as a semiconductor, having a metal-containing surface layer. The metal-containing coating can contain metals, metal oxides, or combinations thereof. A coating of a compound according to Formula I can be applied, for example, to impart anti-soiling characteristics.

In other applications, a coating of a compound according to Formula I is applied to an optical substrate such as those used in doors, windows, picture frames, optical lenses, filters, display devices (e.g., display panels of electronic devices), and the like. For example, the substrate can be an optical component having a metal-containing coating. The metal-containing coating can contain metals, metal oxides, or combinations thereof. In a specific example, the optical component can be a lens with an anti-reflective metal-containing layer. A coating of a compound according to Formula I can be applied to provide anti-soiling resistance. In another specific example, the optical component can be a mirror with a silver-containing coating. The silver-containing coating can contain silver metal, silver oxides, or combinations thereof. A coating of a compound according to Formula I can be applied to the metal-containing surface to provide tarnish resistance.

In some applications, a compound according to Formula I can form a self-assembled monolayer on a substrate. As used herein, the term "self-assembled" refers to spontaneous adsorption of a perfluoropolyether benzotriazole compound to the surface of the substrate. The self-assembled monolayer can be substantially continuous and can be formed by contacting a compound according to Formula I with the surface of the substrate to be treated. The molecules of the compound according to Formula I can form the self-assembled monolayer as a substantially continuous film by virtue of individual molecules of the compound according to Formula I packing together as densely as their molecular structures allow.

The effectiveness of a self-assembled monolayer and the degree to which a self-assembled monolayer is formed on the surface of the metal-containing substrate generally depends on the strength of adsorption of the perfluoropolyether benzotriazole compound to the particular substrate as well as the conditions of use of the self-assembled monolayer. Self-assembled monolayers are generally thin, such as on the order of about 10 nanometers ("nm") or less, and typically do not significantly alter the optical or surface structural properties of the substrate. In many embodiments, the self-assembled monolayer can have a thickness of about 1 nm to about 10 nm. In at least some embodiments, the self-assembled monolayer is about 2 to about 6 nm thick In one method of applying a coating (e.g., a self-assembled monolayer) to a substrate, the coating composition that includes a compound according to Formula I and a suitable solvent (e.g., an alcohol, hydrofluoroether, or combination thereof) is applied to the substrate surface by a conventional coating process, such as spray coating, spin coating, dip coating (immersion), or the like. One exemplary application technique entails immersing the substrate in the coating composition; this technique can reduce solvent emissions and opportunities for scratching or otherwise damaging the substrate. The substrate with the applied coating can then be air dried to remove the solvent, followed by baking in the oven, typically at a temperature of about 100° C. to about 150° C. for about 30 minutes or less, to remove any residual solvent and enhance bonding of the coating to the surface of the substrate.

Although a post treatment process can be included in the method of making the article, such a post treatment process is often not needed if the coating is a self-assembled monolayer. That is, additional post treatment steps such as polishing or solvent washing are often not necessary when the coating is a self-assembled monolayer.

The compounds according to Formula I are often soluble (or dispersible) in hydrofluoroethers such as 3M NOVEC™ Engineered Fluid HFE-7100 (perfluorobutyl methyl ether), which is a mixture of two inseparable isomers with essentially identical physical properties; or other organic solvents such as isopropyl alcohol, ethyl acetate, and acetone. This solubility (or dispersability) allows uniform films of excess material to be applied by spray or spin coating from a solution. The substrate can then be heated to accelerate monolayer formation, and the excess can be rinsed or wiped away to leave the self-assembled monolayer attached to the substrate.

Exemplary compounds according to Formula I that can be applied as a coating, and preferably as a self-assembled monolayer, on a substrate surface include, but are not limited to compounds represented by Formula VI and Formula VII below:

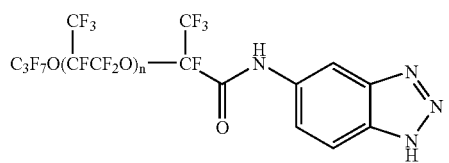

VI

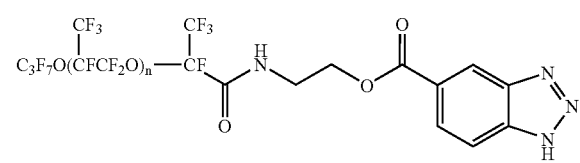

VII where n can have an average value of 0 to 50, 1 to 50, 3 to 30, 3 to 15, or 3 to 10. In some applications, n has a value of at least 3, at least 4, or at least 5.

EXAMPLES

Features and advantages of the present invention are illustrated in the following examples that incorporate particular materials and amounts, and should not be construed as limiting the present invention. All materials are commercially available unless otherwise stated or apparent. All parts, percentages, ratios and the like in the examples are by weight unless otherwise indicated.

Materials Used in the Examples

Unless otherwise noted, all solvents and reagents were or may be obtained from Aldrich Chemical Co. of Milwaukee, Wis. 5-Aminobenzotriazole and benzotriazole-5-carboxylic acid were obtained from Alfa Aesar of Ward Hill, Mass. Copper-, chromium-, and nickel-coated 100 mm diameter silicon wafers were obtained from WaferNet, San Jose, Calif. Deionized water was prepared using a Milli-Q Water System available from Millipore Corporation of Bedford, Mass. As used herein, "HFE 7100" refers to methyl perfluorobutyl ether and is available from 3M Company, St. Paul, Minn. Also, as used herein, "THF" refers to tetrahydrofuran, and "DMF" refers to N,N-dimethylformamide.

Preparative Example 1

Synthesis of

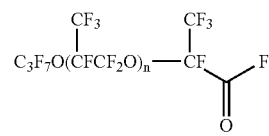

A mixture of hexafluoropropylene oxide oligomers having acyl fluoride groups were prepared essentially as described in U.S. Pat. No. 3,350,808. The mixture (50.3 g) was place into a 450 mL Parr pressure reactor equipped with a bottom drain valve and a cooling jacket. Diethyleneglycol dimethyl ether (11.2 g) and potassium fluoride (2.7 g) were added. The reactor was sealed and cooled to −20° C. using a recirculating refrigeration system. Hexafluoropropylene oxide (HFPO) (167.4 g) was added as a gas into the head space of the reactor over a period of about five hours at a rate of about 0.6 g/minute. The pressure in the reactor at the end of the addition was 24 psig. The resulting mixture was allowed to slowly warm up to ambient temperature while stirring over about 60 hours. The stirrer was turned off and, after about one hour, the lower fluorochemical phase was drained (159 g). This phase contained almost entirely hexafluoropropylene oxide oligomers having acyl fluoride groups. This material was converted to the corresponding oligomeric methyl esters by the addition of anhydrous methanol. The reactor was then cooled to about −20° C. and HFPO (152 g) was added as before but was not treated with methanol. After completion of the reaction, the lower fluorochemical phase was separated as before. This sequence was repeated for an additional four times and the resulting fluorochemical phases from the last five reactions combined. The combined oligomeric acyl fluorides were then fractionally distilled under vacuum. The lower boiling oligomers (through n=2 and including some n=3) were distilled up to a head temperature of 85° C./5 mmHg. The HFPO oligomeric acyl fluorides ($M_N$=994, n=3–8) remaining in the distillation vessel were subsequently used in the preparation of the benzotriazole of Example 1.

Example 1

Preparation of

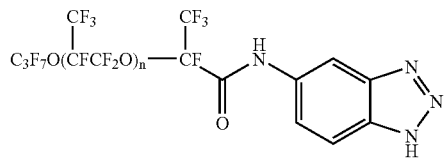

To a magnetically stirred suspension of 5-aminobenzotriazole (5.0 g) in t-butyl methyl ether (125 mL) in a round bottom flask was added triethylamine (3.77 g). To this stirring mixture was added slowly over 30 minutes a mixture of oligomeric perfluoroether acyl fluorides (35 g), the product of the synthesis described in Preparative Example 1. The mixture was stirred overnight at room temperature, after which time 0.4N aqueous HCl (100 mL) was added to the flask. The phases were separated using a separatory funnel and the organic phase was washed once more with 0.4N aqueous HCl. The phases were separated and the volatile components of the organic phase were removed using a rotary evaporator. The residue was dissolved in methanol and the product was precipitated into water to yield a solid. This solid was isolated and was taken up in methanol and the product was again precipitated into water. This process was repeated once more and then the resultant solid was dried in air at room temperature to afford the product as a tan solid. The $^1$H NMR, $^{19}$F NMR and IR spectra of the compounds making up the tan solid product were each consistent with the structural formula provided above.

Preparative Example 2

Synthesis of

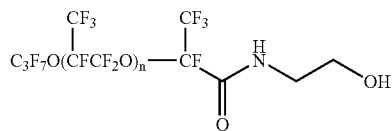

The HFPO derived oligomeric acyl fluorides prepared in a manner similar to that described in Preparative Example 1, can be converted to the corresponding methyl esters by addition of the acid fluoride to anhydrous methanol. The lower fluorochemical phase is separated from the upper methanol phase and washed one to two times with additional methanol and then used without further purification in the synthesis of the HFPO amide alcohol. To the HFPO methyl ester is added all at once about a 30% molar excess of ethanolamine while stirring. The mixture is stirred for a period of four to six hours. A weight of t-butyl methyl ether equal to the weight of starting methyl ester is then added and the resulting solution is washed with 2N hydrochloric acid (using about a 15% molar excess of HCl to the excess ethanolamine left in the reaction mixture) and then water. The t-butyl methyl ether as well as any dissolved water is then removed by distillation at reduced pressure and the resulting amide alcohol is used without further purification.

Example 2

Preparation of

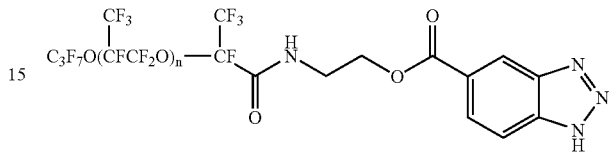

A 250 mL round bottom flask fitted with a reflux condenser and a heating mantle was charged with benzotriazole-5-carboxylic acid (5.0 g), a mixture of oligomeric perfluoroether amido alcohols (38 g) (the product of Preparative Example 2), dry DMF (10 mL), and dry THF (80 mL). As this mixture was magnetically stirred, N,N-dicyclohexylcarbodiimide (6.3 g) and 4-(N,N-dimethylamino)pyridine (0.6 g) were added to the flask. The mixture was stirred and heated at reflux for 2 days. The mixture was allowed to cool to room temperature and then the volatile components were removed using a rotary evaporator. The residue was partially purified by column chromatography on silica gel using 70:30 (v/v) hexane/ethyl acetate as the eluting solvent. The isolated brown material was concentrated using a rotary evaporator and the residue was dissolved in ethyl acetate (150 mL) and this solution was washed twice with water (50 mL). The organic phase was dried over $MgSO_4$ and was then filtered. The volatile components were removed using a rotary evaporator. The product (31.7 g) was isolated after three recrystallizations from ethyl acetate. The $^1$H NMR, $^{19}$F NMR and IR spectra of the compounds making up the product were each consistent with the structural formula provided above.

Examples 3–10

Contact Angles of Water on Treated Metal Surfaces

The product prepared in Example 1 was diluted with isopropyl alcohol to a concentration of 0.2 weight percent, and with HFE 7100 to a concentration of 0.1 weight percent to prepare two coating solutions. Pieces of one quarter of each of copper-, chromium-, and nickel-coated silicon wafers were cleaned by 5-minute exposure in a UV/ozone chamber. The UV/ozone chamber contained an ultraviolet lamp measuring 5 inches by 5 inches (12.5 cm by 12.5 cm) (obtained under the trade designation "UV GRID LAMP", model 88-9102-02 from BHK of Claremont, Calif.), and which was encased in a small sheet metal box (13 cm wide by 14 cm deep by 15 cm wide) such that the lamp was suspended 8 cm above the bottom of the box. A small lab jack was used to position metal wafer pieces to be cleaned as close as possible to the ultraviolet lamp without physically contacting the lamp. The front of the box was a door, hinged at the top that allowed samples to be inserted and removed. An oxygen source was attached to a small hole in one side of the box that provided oxygen to the box at a rate of approximately 1 to 5 standard liters per minute.

The pieces of metal-coated silicon wafer were treated with the solutions of the product prepared in Example 1 by one of the following methods. The first method involved immersing pieces of metal-coated silicon wafers in the respective solutions for 1 hour and then rinsing with the solvent and drying under a stream of nitrogen gas. The second method involved spin-coating the metal-coated silicon wafers with the respective solutions using a CEE Model 100 spin coater (obtained from Brewer Science of Rolla, Mo.) first at 500 rpm for 5 seconds and then at 2000 rpm for 15 seconds, heating the coated wafer on a CEE Model 1100 vacuum hotplate (available from Brewer Science of Rolla, Mo.) having a surface temperature of 150° C. for 3 minutes, rinsing the wafer with the solvent, and then drying the wafer under a stream of nitrogen gas. Static, advancing, and receding contact angles of deionized water on the treated surfaces were measured using a Model VCA-2500XE video contact angle analyzer (available from AST Products, Billerica, Mass.) and drop volumes of 5 microliters for the advancing contact angle measurements and 1–3 microliters for the advancing and receding contact angle measurements. The data are given in Table 1. In Table 1, "IPA" means isopropyl alcohol, "HFE" means HFE 7100, "S" refers to the static contact angle, "A" refers to the advancing contact angle, "R" refers to the receding contact angle, and the metal-coated silicon wafers are identified by the element symbol for the metal. For comparison as controls, water contact angles on cleaned uncoated metal wafers were too low to measure (less than 20°).

TABLE 1

Water Contact Angle Data of Examples 3–10

| EXAMPLE | SOLVENT | METAL COATING | PREPARATION METHOD | WATER CONTACT ANGLES (S, A, R) |
| --- | --- | --- | --- | --- |
| 3 | IPA | Cu | Immersion | 120°, 126°, 116° |
| 4 | IPA | Cr | Spin coating | 136°, 145°, 115° |
| 5 | HFE | Cu | Immersion | 120°, 123°, 113° |
| 6 | HFE | Cu | Spin coating | 117°, 127°, 101° |
| 7 | HFE | Cr | Immersion | 118°, 121°, 50° |
| 8 | HFE | Cr | Spin coating | 136°, 143°, 114° |
| 9 | HFE | Ni | Immersion | 124°, 135°, 109° |
| 10 | HFE | Ni | Spin coating | 124°, 134°, 113° | vacuum hotplate (available from Brewer Science of Rolla, Mo.), having a surface temperature of 150° C., for 3 minutes, rinsing the wafer with the solvent, and then drying the wafer under a stream of nitrogen gas. Advancing and receding contact angles of hexadecane on the treated surfaces were measured using a Model VCA-2500XE video contact angle analyzer (available from AST Products, Billerica, Mass.) and drop volumes of 1–3 microliters. The data are given in Table 2. In Table 2, "A" refers to the advancing contact angle, "R" refers to the receding contact angle, and the metal-coated silicon substrates are identified by the element symbol for the metal. For comparison as controls, hexadecane contact angles on cleaned uncoated metal wafers were too low to measure (less than 20°).

TABLE 2

Hexadecane Contact Angle Data of Examples 11–16

| EXAMPLE | METAL COATING | PREPARATION METHOD | HEXADECANE CONTACT ANGLES (A, R) |
| --- | --- | --- | --- |
| 11 | Cu | Immersion | 76°, 65° |
| 12 | Cu | Spin coating | 77°, 62° |
| 13 | Cr | Immersion | 82°, 38° |
| 14 | Cr | Spin coating | 85°, 48° |
| 15 | Ni | Immersion | 79°, 63° |
| 16 | Ni | Spin coating | 80°, 59° |

Example 11–16

Contact Angles of Hexadecane on Treated Metal Surfaces

A solution of the product prepared in Example 1 was made by diluting the product in HFE 7100 to a concentration of 0.1 weight percent. Pieces of one quarter of each of the cooper-, chromium-, and nickel-coated silicon wafers were cleaned by 5-minute exposure in a UV/ozone chamber as described in Examples 3–10. The pieces of metal-coated silicon wafer were treated with the solution of the product prepared in Example 1 by one of the following methods. The first method involved immersing a piece of metal oxide-coated silicon wafer in the solution for 1 hour and then rinsing with the solvent and drying under a stream of nitrogen gas. The second method involved spin-coating the metal-coated wafer with the solution using a CEE Model 100 spin coater (obtained from Brewer Science of Rolla, Mo.) first at 500 rpm for 5 seconds and then at 2000 rpm for 15 seconds, heating the coated wafer on a CEE model 1100

Examples 17–18

Contact Angles of Water and Hexadecane on Treated Metal Surfaces

A solution of the product prepared in Example 2 was made by diluting the product in HFE 7100 to a concentration of 0.1 weight percent. Pieces of one quarter of each of the copper-, chromium-, and nickel-coated silicon wafers were cleaned by 5-minute exposure in a UV/ozone chamber as described in Examples 3–10. The pieces of metal-coated silicon wafer were treated with the solution of the product of Example 2 using one of the following methods. The first method involved immersing the piece of copper-coated wafer in the solution for 1 hour and then rinsing with the solvent and drying under a stream of nitrogen gas. The second method involved spin-coating the chromium-coated wafer with the solution using a CEE Model 100 spin coater (obtained from Brewer Science of Rolla, Mo.) first at 500 rpm for 5 seconds and then at 2000 rpm for 15 seconds, heating the coated wafer on a CEE model 1100 vacuum hotplate (available from Brewer Science of Rolla, Mo.), having a surface temperature of 150° C., for 3 minutes, rinsing the wafer with the solvent, and then drying the wafer under a stream of nitrogen gas. Static, advancing, and receding contact angles of deionized water, and advancing and receding contact angles of hexadecane were measured on the treated surfaces using a Model VCA-2500XE video contact angle analyzer (available from AST Products, Billerica, Mass.) and drop volumes of 5 microliters for the static contact angle measurements and 1–3 microliters for the advancing and receding contact angle measurements. The data are given in Table 3. In Table 3, "S" refers to the static contact angle, "A" refers to the advancing contact angle, "R" refers to the receding contact angle, and the metal-coated silicon substrates are identified by the element symbol for the metal. For comparison as controls, contact angles on cleaned uncoated metal wafers were too low to measure (less than 20°).

TABLE 3

Hexadecane and Deionized Water Contact Angle Data of Examples 17–18

| EXAMPLE | METAL COATING | PREPARATION METHOD | HEXADECANE CONTACT ANGLES (A, R) | WATER CONTACT ANGLES (S, A, R) |
| --- | --- | --- | --- | --- |
| 17 | Cu | Immersion | 75°, 64° | 122°, 126°, 104° |
| 18 | Cr | Spin coating | 83°, 53° | 133°, 142°, 117° |

Although the present invention has been described with reference to preferred embodiments, workers skilled in the art will recognize that changes may be made in form and detail without departing from the spirit and scope of the invention.

We claim:

1. A compound according to Formula I:

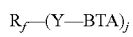

wherein $R_f$ is a monovalent or divalent perfluoropolyether group, wherein the perfluoropolyether group has at least two catenated oxygen atoms;

Y is —NH—(CO)—;

j is 1 or 2; and

BTA is a monovalent benzotriazolyl group selected from

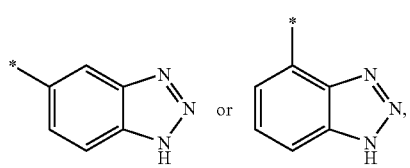

wherein the benzotriazolyl group is unsubstituted or substituted with an alkyl, alkoxy, or combination thereof.

2. The compound of claim 1, wherein $R_f$ is monovalent and the compound is of Formula II:

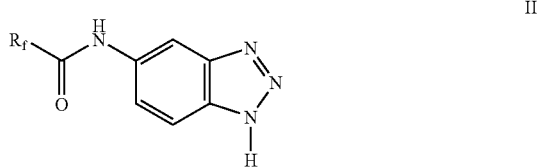

3. A compound according to Formula II of claim 2, the compound represented by Formula VI:

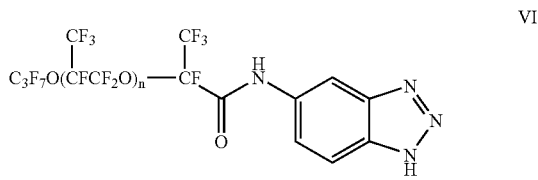

where n in an integer of 0 to 50.

4. A composition comprising (a) a solvent selected from an alcohol, ester, ketone, fluorinated hydrocarbon, ether, and hydrochlorofluoro alkane, or mixtures thereof; and (b) a compound according to Formula I:

wherein $R_f$ is a monovalent or divalent perfluoropolyether group, wherein the perfluoropolyether group has at least two catenated oxygen atoms;

Y is —NH—(CO)—;

j is 1 or 2; and

BTA is a monovalent benzotriazolyl group selected from

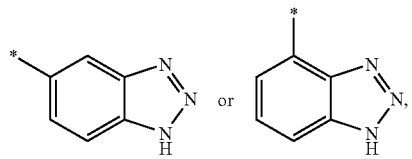

wherein the benzotriazolyl group is unsubstituted or substituted with an alkyl, alkoxy, or combination thereof.-

5. The composition of claim 4 wherein the solvent comprises a hydrofluoroether represented by Formula VIII:

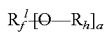   VIII wherein
a is an integer ranging from 1 to 3;
the group $R_f^1$ is a monovalent, divalent, or trivalent moiety derived from a perfluoroalkane, perfluoroether, or perfluoropolyether;
$R_h$ is an alkyl or heteroalkyl; and
the sum of the number of carbon atoms in the group $R_f^1$ and the number of carbon atoms in the group $R_h$ is greater than or equal to four.

6. An article comprising a substrate and a compound attached to a surface of the substrate, the compound being according to Formula I:

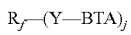   I wherein
$R_f$ is a monovalent or divalent perfluoropolyether group, wherein the perfluoropolyether group has at least 5 two catenated oxygen atoms;
Y is —NH—(CO)—;
j is 1 or 2; and
BTA is a monovalent benzotriazolyl group selected from

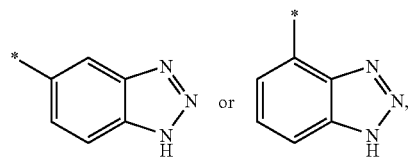

wherein the benzotriazolyl group is unsubstituted or substituted with an alkyl, alkoxy, or combination thereof.

7. The article of claim 6 wherein $R_f$ is monovalent and the compound is represented by Formula II:

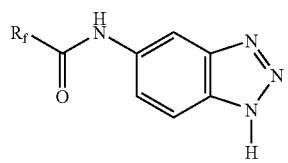   II

8. The article of claim 7 wherein the compound according to Formula II is represented by Formula VI:

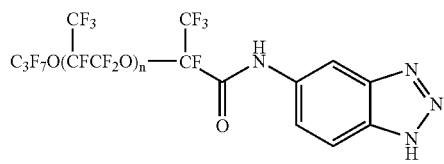   VI where n is an integer of 0 to 50.

9. The article of claim 6 wherein the substrate has an outer surface comprising a metal oxide.

10. A method of making an article, the method comprising
providing a substrate;
applying a coating composition to a surface of the substrate, the coating composition comprising a compound according to Formula I:

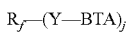   I wherein
$R_f$ is a monovalent or divalent perfluoropolyether group, wherein the perfluoropolyether group has at least two catenated oxygen atoms;
Y is —NH—(CO)—;
j is 1 or 2; and
BTA is a monovalent benzotriazolyl group is selected from

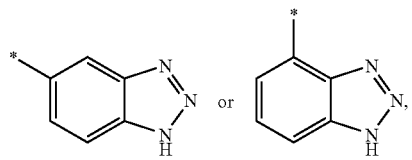

wherein the benzotriazolyl group is unsubstituted or substituted with an alkyl, alkoxy, or combination thereof.

11. The method of claim 10 wherein the substrate has an outer surface comprising a metal oxide.

12. A method of treating a substrate, the method comprising
providing a substrate;
applying a coating composition to a surface of the substrate, the coating composition comprising a compound according to Formula I:

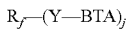   I wherein
$R_f$ is a monovalent or divalent perfluoropolyether group, wherein the perfluoropolyether group has at least two catenated oxygen atoms;
Y is —NH—(CO)—;
j is 1 or 2; and
BTA is a monovalent benzotriazolyl group is selected from

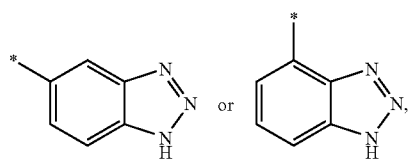

wherein the benzotriazolyl group is unsubstituted or substituted with an alkyl, alkoxy, or combination thereof.

13. The method of claim 12 wherein the substrate has an outer surface comprising a metal oxide.

* * * * *

UNITED STATES PATENT AND TRADEMARK OFFICE
CERTIFICATE OF CORRECTION

PATENT NO. : 7,148,360 B2
APPLICATION NO. : 10/769024
DATED : December 12, 2006
INVENTOR(S) : Richard M. Flynn It is certified that error appears in the above-identified patent and that said Letters Patent is hereby corrected as shown below:

Column 5 – Line 58 (Approx.) - After "to 15," insert -- or --.

Column 5 – Line 28 (Approx.) - Delete "–$CF_2CF(Z)O$)" – and insert -- –($CF_2CF(Z)O$)– --, therefor.

Column 6 – Line 3 - Delete "O)n CF(CF3)—" and insert -- O)nCF(CF3)— --, therefor. (Consider space)

Column 8 – Line 15 - Delete "O" and insert -- 0 --, therefor.

Column 8 – Line Structure VIII - Delete " $R_f^1\!\!-\!\![O\!-\!R_h]_a$ " and insert -- $R_f^1\!\!-\!\![O\!-\!R_h]_a$ --, therefor.

Column 10 – Line 9 - Delete "amino-benzotriazole," and insert -- aminobenzotriazole, --, therefor.

Column 13 – Line 9 - After "thick" insert -- . --.

Column 17 – Line 48 (Approx.) - Delete "Example" and insert -- Examples --, therefor.

Column 17 – Line 55 - Delete "cooper–," and insert -- copper–, --, therefor.

Column 20 – Line 42 - In Claim 3, after "where n" delete "in" and insert -- is --, therefor.

Column 20 – Line 48 (Approx.) - In Claim 4, delete "$R_f$—(Y—BTA)$_f$;" and insert -- $R_f$—(Y—BTA)$_j$ --, therefor.

Column 20 – Line 67 (Approx.) - In Claim 4, delete "thereof.-" and insert -- thereof. --, therefor.

UNITED STATES PATENT AND TRADEMARK OFFICE
CERTIFICATE OF CORRECTION

PATENT NO.         : 7,148,360 B2
APPLICATION NO.    : 10/769024
DATED              : December 12, 2006
INVENTOR(S)        : Richard M. Flynn It is certified that error appears in the above-identified patent and that said Letters Patent is hereby corrected as shown below:

Column 21 – Line 3 - In Claim 5, delete " $R_f^1\text{-}[O\text{---}R_h]_a$ " and insert -- $R_f^1\text{-}[\text{-}O\text{---}R_h]_a$ --, therefor.

Column 21 – Line 20 (Approx.) - In Claim 6, after "at least" delete "5".

Signed and Sealed this

Second Day of December, 2008

JON W. DUDAS
*Director of the United States Patent and Trademark Office*